(12) United States Patent
Stahl et al.

(10) Patent No.: US 6,495,027 B1
(45) Date of Patent: Dec. 17, 2002

(54) ELECTROCHEMICAL GAS SENSOR AND METHOD FOR DETERMINING GAS COMPONENTS

(75) Inventors: Roland Stahl, Freiberg (DE); Thomas Brinz, Bissingen (DE); Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/786,407
(22) PCT Filed: Jun. 30, 2000
(86) PCT No.: PCT/DE00/02141
§ 371 (c)(1), (2), (4) Date: Apr. 27, 2001
(87) PCT Pub. No.: WO01/02845
PCT Pub. Date: Jan. 11, 2001

(30) Foreign Application Priority Data

Jul. 2, 1999 (DE) .......................... 199 30 636

(51) Int. Cl.$^7$ ............................................. G01N 27/407
(52) U.S. Cl. ........................ 205/781; 205/784; 204/425; 204/426; 204/427; 73/23.31
(58) Field of Search ................................. 204/424, 425, 204/426, 427, 428; 205/781, 783.5, 784, 784.5; 73/23.31

(56) References Cited

U.S. PATENT DOCUMENTS

| | | | |
|---|---|---|---|
| 5,322,601 A | | 6/1994 | Liu et al. |
| 5,861,092 A | * | 1/1999 | Kiyota et al. ............... 204/425 |
| 6,045,673 A | * | 4/2000 | Kato et al. ................... 204/425 |
| 6,068,747 A | * | 5/2000 | Tojo et al. ................... 204/424 |

FOREIGN PATENT DOCUMENTS

| | | | |
|---|---|---|---|
| EP | 0 678 740 | | 10/1995 |
| GB | 2288873 | * | 1/1995 |
| WO | WO 94/02845 | | 2/1994 |
| WO | 96/17242 | * | 6/1996 |

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

An electrochemical gas sensor and a method for determining the concentration of gaseous components in a gas mixture, particularly of $NO_x$ in exhaust gases of internal combustion engines. The gas sensor includes a first measuring-gas compartment which is in communication with the measuring gas, and two additional measuring-gas compartments which are connected to the first measuring-gas compartment via diffusion barriers. The first measuring-gas compartment contains a first pump cell which, with the aid of pump electrodes arranged on a solid electrolyte, transports oxygen into and out of the measuring-gas compartment. The second and third measuring-gas compartments contain further pump cells, the second measuring-gas compartment being used for measuring the oxygen concentration of the mixture, and the third measuring-gas compartment being used for measuring the sum of the oxygen concentration and the concentration of the gaseous component in the gas mixture. The pump current measured between two pump electrodes arranged on a solid electrolyte is used by both amperometric measuring pump cells as a measured quantity, and a measuring signal proportional to the concentration of the gaseous component to be determined is obtained through subtraction of both pump currents.

12 Claims, 3 Drawing Sheets

ELECTROCHEMICAL GAS SENSOR AND METHOD FOR DETERMINING GAS COMPONENTS

FIELD OF THE INVENTION

The present invention relates to an electrochemical gas sensor and a method for determining gaseous components.

BACKGROUND INFORMATION

The European Patent Application No. 0 678 740 discusses a gas sensor for determining the $NO_x$ concentration in a gas mixture, in which two measuring-gas compartments, each having a pump cell, are arranged one behind the other in one layer plane of a planar, oxygen-ion-conducting, ceramic carrier. The measuring gas streams via a first diffusion opening into the first measuring-gas compartment in which a first inner pump electrode is arranged. An outer pump electrode is exposed directly to the exhaust-gas compartment. The first inner pump electrode and the outer pump electrode form the first pump cell. A predetermined oxygen partial pressure is adjusted in the first measuring-gas compartment by pumping oxygen in and out with the aid of the first pump cell. A concentration cell (Nernst cell) has a measuring electrode and a reference electrode in communication with an air atmosphere, the measuring electrode being disposed in the first measuring-gas compartment. To set a constant oxygen partial pressure in the first measuring-gas compartment, the electric voltage (electromotive force) of the concentration cell is adjusted to a constant value by a pump voltage of the first pump cell. The first and second measuring-gas compartments are connected with a connecting duct which represents a further diffusion opening, the atmosphere that is set to a constant oxygen partial pressure being diffused into the second measuring compartment via the connecting duct. Disposed in the second measuring-gas compartment is a further inner pump electrode which cooperates with the reference electrode arranged in the air-reference duct and forms the second pump cell. The further inner pump electrode is constructed of a material, e.g., of rhodium, which produces a decomposition of NO to $N_2$ and $O_2$. The reduced oxygen obtained at the further inner pump electrode is pumped in ion form via an applied pump voltage to the reference electrode and is released there into the air atmosphere. Since the atmosphere in the first measuring-gas compartment is retained at a constant oxygen partial pressure, the pump current for evacuating the reduced oxygen from the second measuring-gas compartment is proportional to the $NO_x$ concentration.

The sensor-element design is believed to be relatively complicated and the measuring accuracy is believed to be dependent on many factors, such as the exact adjustment of the measuring temperature and the oxygen partial pressure.

SUMMARY OF THE INVENTION

The exemplary gas sensor and the exemplary method of the present inventions are believed to have the advantage that, because of the sensor design and the measuring method utilized, the concentration of the gaseous component to be measured is yielded in a very simple manner which is nevertheless sufficiently accurate. The exemplary gas sensor according to the present invention includes a first pump cell and two additional measuring pump cells likewise functioning according to the amperometric measuring principle. Since both measuring pump cells are operated according to the same amperometric measuring principle, a particular advantage of the exemplary device and exemplary method of the present inventions is believed to involve the fact that a measuring signal proportional to the concentration of the gaseous components to be determined is obtained with great accuracy through simple subtraction of the pump currents of both amperometric measuring pump cells.

In other exemplary embodiments, the spatially confined arrangement of the two electrochemical measuring pump cells allows a simple and temperature-compensated measurement. Furthermore, the common outer pump electrode of the two measuring pump cells can be arranged in direct contact with the ambient air, but for that purpose, the integration of an air-reference duct into the layer system of the sensor element may be necessary. However, the measuring based on determining pump currents also permits the arrangement of the outer pump electrode in the same atmosphere as the measuring-gas, and consequently allows for the omission of an air-reference duct. It is believed that this should simplify the design of the sensor element substantially, and should represent a great cost savings.

DETAILED DESCRIPTION

Figure 1:
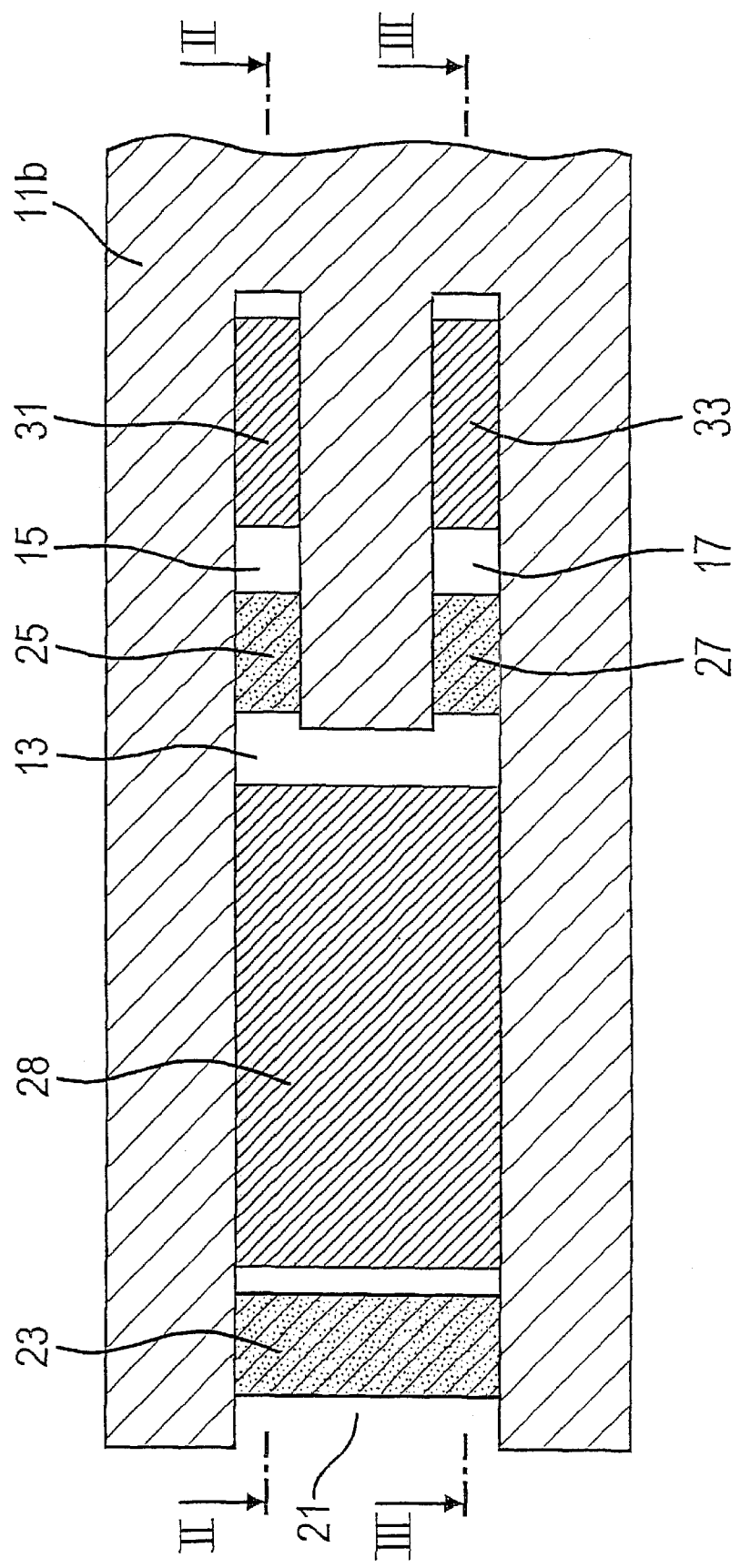
FIG. 1 shows a cross-section through the large area of the sensor element according to an exemplary embodiment of the present invention.
Figure 2:
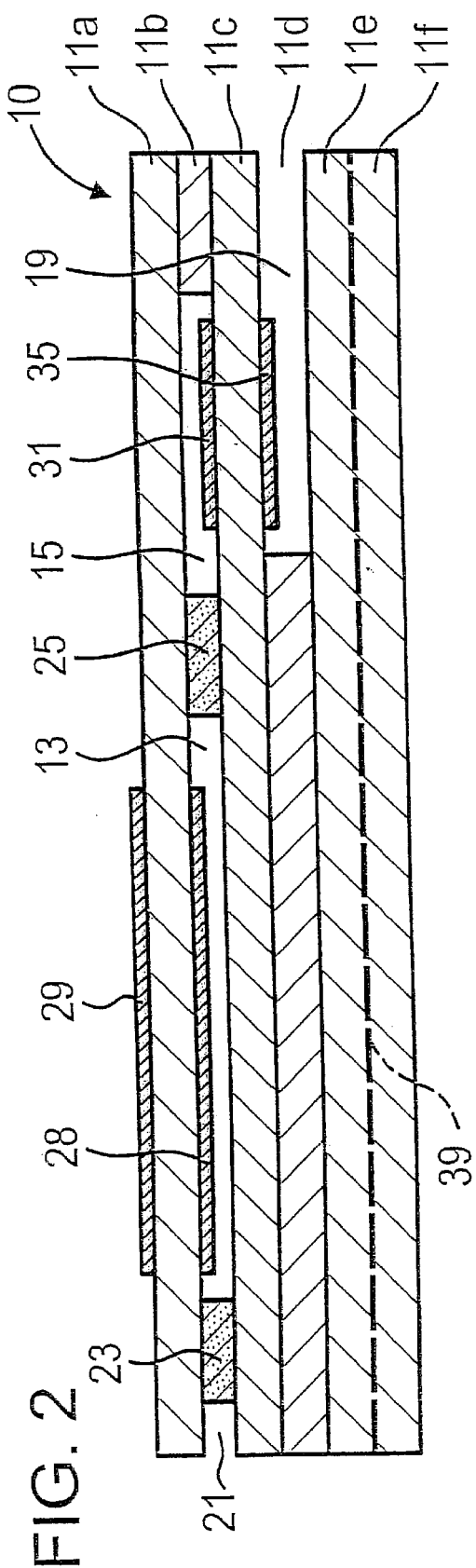
FIG. 2 shows a longitudinal section through the sensor element according to line II—II in FIG. 1.
Figure 3:
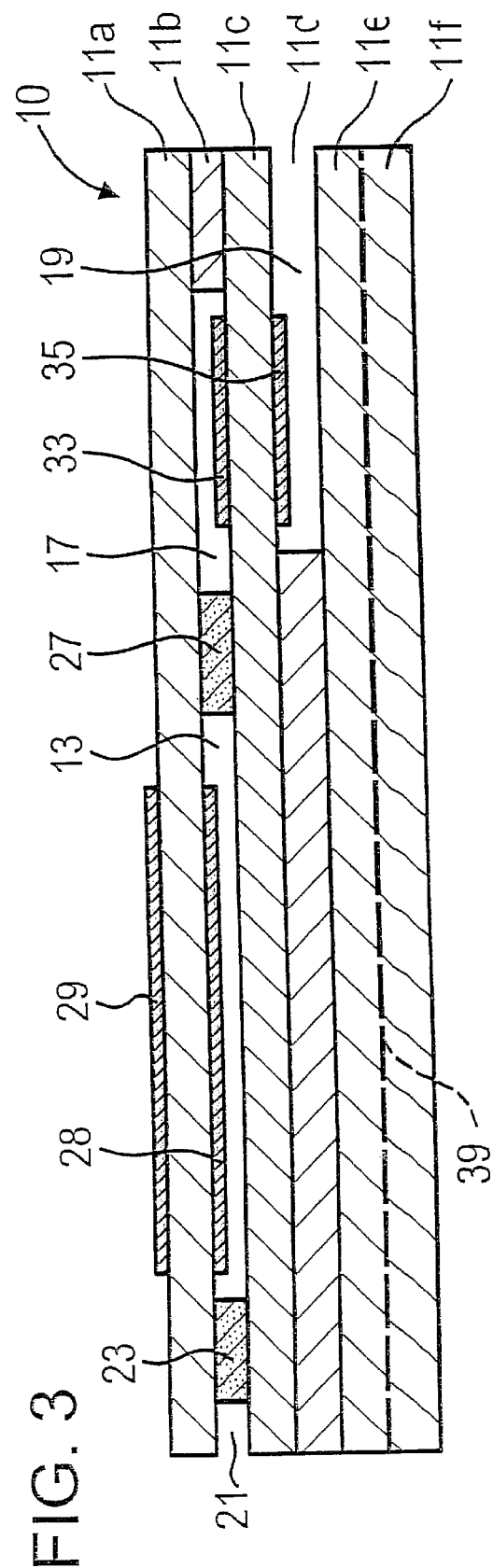
FIG. 3 shows a longitudinal section through the sensor element according to line III—III in FIG. 1.

FIGS. 1, 2 and 3 show a first exemplary embodiment of the present invention. Numeral 10 designates a planar sensor element of an electrochemical gas sensor that has, for example, a plurality of oxygen-ion-conducting solid electrolyte layers 11a, 11b, 11c, 11d, 11e and 11f. Solid electrolyte layers 11a–11f are constructed from ceramic foils and form a planar ceramic body. The integrated form of the planar ceramic body of sensor element 10 is produced by laminating together the ceramic foils imprinted with functional layers, and subsequently sintering the laminated structure in an available manner. Each of the solid electrolyte layers 11a–11f is constructed from an oxygen-ion-conducting solid electrolyte material such as stabilized $ZrO_2$.

Sensor element 10 also includes a first measuring-gas compartment 13 and two additional measuring-gas compartments 15 and 17, all three measuring-gas compartments being formed in the same electrolyte layer. For example, the two additional measuring-gas compartments 15, 17 are disposed side-by-side in parallel, and in each case extend in the form of a duct which itself begins at first measuring-gas compartment 13. The first measuring gas-compartment 13 is separated from the additional measuring-gas compartments 15, 17 by diffusion barriers 25 and 27. Arranged independently from measuring-gas compartments 13, 15 and 17 is an air reference dust 19. For example, in the embodiment shown in FIGS. 1, 2 and 3, the air reference duct 19 is located in a different electrolyte layer than measuring-gas compartments 13, 15 and 17. One end of air reference duct 19 is open to the atmosphere and is in communication with atmospheric air.

Sensor element 10 also has a gas-intake port 21 which guides the measuring gas into first measuring-gas compartment 13. Gas-intake port 21 is arranged, for example in FIGS. 1, 2 and 3, in the same electrolyte layer as measuring-gas compartments 13, 15 and 17. Downstream of gas-intake port 21 in the direction of flow of the measuring gas, separating the gas-intake port 21 from measuring-gas compartment 13, is a first diffusion barrier 23 made from, for example, porous ceramic material. Further diffusion barriers 25 and 27, respectively, are located between measuring-gas compartments 13 and 15 and between measuring-gas compartments 13 and 17 continuing in the direction of the flow of the measuring gas.

A first inner electrode 28 is arranged in first measuring-gas compartment 13 disposed at the inner side of electrolyte layer 11a. Disposed at the outer side of electrolyte layer 11a in direct contact with the measuring gas is an outer electrode 29 which can also be covered with a porous protective layer, not shown. Located in second and third measuring-gas compartments 15 and 17 are further inner electrodes 31 and 33, respectively. Common outer electrode 35 belonging to them is situated in air-reference duct 19.

To better ensure that no decomposition of gaseous components occurs at the electrodes in measuring-gas compartments 13 and 15, electrodes 28 and 31 arranged therein are made, for example, of a gold/platinum alloy. In third measuring-gas compartment 17, on the other hand, a material which, for example, can effect the catalytic decomposition of $NO_x$ into oxygen and nitrogen is used for electrode 33. For example, rhodium or a platinum/rhodium alloy is suitable for this purpose. Outer electrodes 29, 35 are made of a catalytically active material, e.g. of platinum. In this context, the electrode material for all the electrodes is used, in an available manner, as ceramic to permit sintering with the ceramic foils.

Furthermore, embedded in the ceramic foundation of sensor element 10 between two electrical insulating layers, not shown here, is a resistance heater 39. The resistance heater is used to heat up sensor element 10 to the necessary operating temperature. In this context, essentially the same temperature exists at the spatially closely adjacent electrodes 28, 29, 31, 33 and 35.

When operating or using the sensor element 10 as an $NO_x$ sensor, outer electrode 29 and first inner electrode 28 are operated in an exemplary method as pump electrodes of a first pump cell. At these electrodes, a pump current is generated by which a constant oxygen partial pressure (e.g. 1000 ppm) is set in first measuring-gas compartment 13 by pumping oxygen in or out. The gas to be measured measuring atmosphere, adjusted to a constant oxygen partial pressure, in measuring-gas compartment 13 now comes via diffusion barriers 25 and 27 into second and third measuring-gas compartments 15 and 17, respectively. Located in second measuring-gas compartment 15 is second inner electrode 31 which, together with reference electrode 35, is operated as a second pump cell. The first pump cell is used to control the oxygen partial pressure adjusted in measuring-gas compartment 13. In this context, the pump voltage applied at electrodes 28 and 29 is regulated in such a way or so that a constant pump current appears at the second pump cell. When working with a lean measuring gas (lambda>1), oxygen is pumped out of first measuring-gas compartment 13 by the first pump cell, whereas when working with a rich measuring gas (lambda<1), oxygen is pumped into the first measuring-gas compartment. The selection of the appropriate oxygen partial pressure and of the electrode material ensures that no oxygen resulting from the catalytic decomposition of $NO_x$ at electrodes 28 and 31 is evacuated.

Arranged in third measuring-gas compartment 17 is third inner electrode 33 which, together with reference electrode 35, is likewise operated as a pump cell. Because of the catalytic material, third inner electrode 33 functions as an $NO_x$-sensitive electrode at which the $NO_x$ is decomposed according to the reaction $NO_x \rightarrow \frac{1}{2}N_2 + x/2O_2$. The pump current occurring in this context represents a measure for the sum of free oxygen and oxygen evacuated by catalytic decomposition of $NO_x$. A measuring signal proportional to the $NO_x$ concentration is obtained through simple subtraction of the limiting currents measurable at the second and third pump cells in measuring-gas compartments 15 and 17.

Should compensating currents appear between outer electrodes 29, 35 in the above-described gas sensor, then the relevant solid electrolyte layers must be electrically interrupted (or isolated) by incorporating suitable insulating intermediate layers. In this case, inner electrodes 28, 31 and 33 can be combined to form a continuous electrode, i.e., can be operated via a common connection contact.

Figure 4:
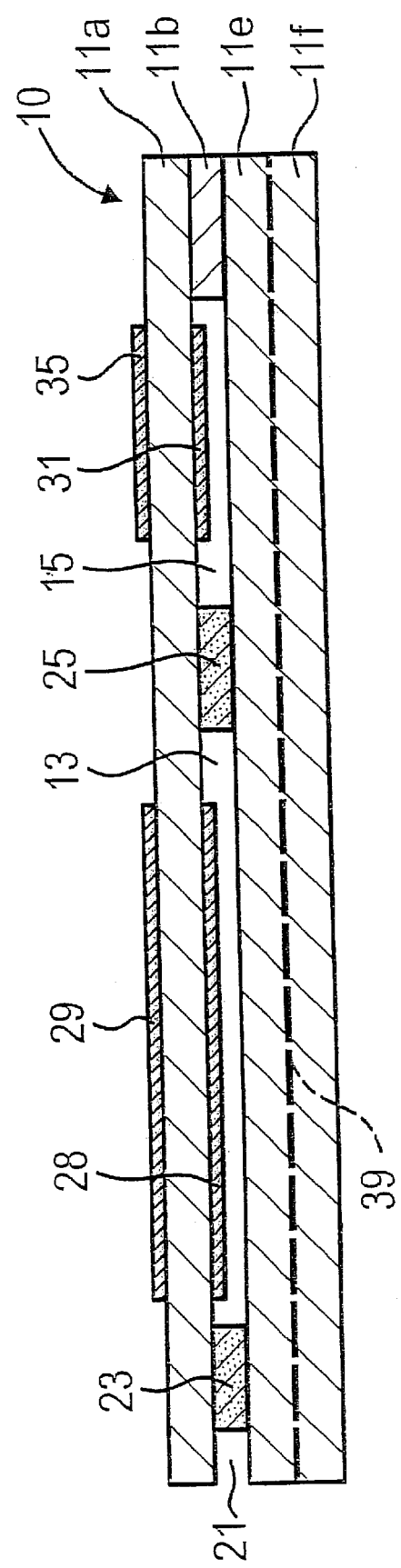
FIG. 4 shows a longitudinal section through the sensor element according to a further exemplary embodiment.

In another exemplary embodiment of the present invention, outer electrode 35 is not, as shown in FIGS. 2 and 3, arranged in air-reference duct 19, but is instead arranged directly on solid electrolyte layer 11a of the sensor element according to FIG. 4, so that electrode 35 is likewise exposed to the measuring gas. This makes it unnecessary to incorporate air-reference duct 19 into the layer system, thus substantially simplifying the design of the sensor element.

What is claimed is:

1. A gas sensor for determining a concentration of gaseous components of a gas mixture having at least $NO_x$ in an exhaust gas of an internal combustion engine, the gas sensor comprising:

a sensor body formed from a plurality of oxygen-ion-conducting solid electrolyte layers;

a first measuring-gas compartment formed within said sensor body;

a first pump cell comprising at least one inner pump electrode within said first measuring-gas compartment disposed on a solid electrolyte layer and at least one outer pump electrode disposed on an opposite side of said solid electrolyte layer, said first pump cell used for transporting oxygen one of into and out of said first measuring-gas compartment;

a second measuring-gas compartment formed within said sensor body, wherein a gas mixture can flow directly from said first measuring-gas compartment into said second measuring-gas compartment;

a second pump cell comprising at least one inner pump electrode within said second measuring-gas compartment disposed on a solid electrolyte layer and at least one outer pump electrode disposed on an opposite side of said solid electrolyte layer, said second pump cell used for transporting oxygen one of into and out of said second measuring-gas compartment;

a third measuring-gas compartment formed within said sensor body, wherein a gas mixture can flow directly from said first measuring-gas compartment to said third measuring-gas compartment; and a third pump cell comprising at least one inner pump electrode within said third measuring-gas compartment disposed on a solid electrolyte layer and at least one outer pump electrode disposed on an opposite side of said solid electrolyte layer, wherein the at least one inner pump electrode is selected from a material that catalytically decomposes $NO_x$ into at least oxygen, said third pump cell used for transporting oxygen one of into and out of said third measuring-gas compartment;

wherein said second pump cell and said third pump cell generate a measurable pump current corresponding to the oxygen concentration within their respective measuring-gas compartments.

2. The gas sensor of claim 1, wherein:
said first, second and third pump cells are arranged with said inner pump electrodes all within one solid electrolyte layer of said sensor body.

3. The gas sensor of claim 2, wherein said second and said third measuring-gas compartments are arranged side-by-side and parallel to each other within a single solid electrolyte layer of said sensor body.

4. The gas sensor of claim 2, wherein at least one diffusion barrier, through which a gas mixture containing $NO_x$ can diffuse, separates said first measuring-gas compartment from said second measuring-gas compartment, and at least one diffusion barrier, through which a gas mixture containing $NO_x$ can diffuse, separates said first measuring-gas compartment from said third measuring-gas compartment.

5. The gas sensor of claim 4, wherein at least one diffusion barrier, through which a gas mixture containing $NO_x$ can diffuse, separates said first measuring-gas compartment from the atmosphere containing the gas to be measured.

6. The gas sensor of claim 1, wherein said outer pump electrode of said second pump cell and said outer pump electrode of said third pump cell are connected to form a single reference electrode.

7. The gas sensor of claim 6, wherein said reference electrode is located within an air-reference duct which itself is in direct contact with atmospheric air.

8. The gas sensor of claim 1, wherein said outer electrodes of said second pump cell and said third pump cell are in direct contact with atmospheric air.

9. The gas sensor of claim 1, wherein said second pump cell and said third pump cell are spatially arranged at equivalent distances from said first measuring-gas compartment so that they are subject to comparable temperature conditions.

10. The gas sensor of claim 1, wherein the inner pump electrode of the third pump cell is made of at least one of rhodium and an alloy of rhodium an d platinum.

11. The gas sensor of claim 1, wherein said outer electrodes of said second pump cell and said third pump cells are each located within an air reference duct which itself is in direct contact with atmospheric air.

12. A method for determining a concentration of a gaseous component of a gas mixture having at least $NO_x$ in an exhaust gas of an internal combustion engine, the method comprising the steps of:

placing a gas sensor formed from a plurality of oxygen-ion-conducting solid electrolyte layers into a gas mixture, wherein said gas sensor comprises:
at least three pump cells each comprising at least one measuring-gas compartment formed within said solid electrolyte layers; at least one inner pump electrode within each said measuring-gas compartments disposed on a solid electrolyte layer; at least one outer pump electrode disposed on the opposite side of the respective said inner pump electrode and on said solid electrolyte layer wherein at least one inner pump electrode is made from a material that catalytically decomposes the gaseous component to be measured into at least oxygen; said pump cells being used for transporting oxygen into and out of said measuring-gas compartments and at least two of said pump cells each generating a measurable pump current corresponding to an amount of oxygen within their respective measuring-gas compartments; wherein said gas sensor first adjusts an oxygen concentration of the gas mixture to a constant value in at least one of said measuring-gas compartments using at least one of said pump cells;

measuring said measurable pump currents from said pump cells;

calculating a difference between said measurable pump currents from said gas sensor to determine an amount of oxygen resulting from the reduction of oxygen contained within the gaseous component of the gas mixture; and calculating the concentration of a gaseous component to be determined using said calculated amount of reduced oxygen.

* * * * *